United States Patent
Yamakawa et al.

(10) Patent No.: US 7,629,118 B2
(45) Date of Patent: Dec. 8, 2009

(54) METHOD OF TESTING WHEAT

(75) Inventors: Hirohito Yamakawa, Saitama (JP); Eriko Suzuki, Saitama (JP); Kiyoko Miyatake, Saitama (JP); Katsuyuki Hayakawa, Saitama (JP)

(73) Assignee: Nisshin Seifun Group Inc., Tokyo (JP)

( * ) Notice: Subject to any disclaimer, the term of this patent is extended or adjusted under 35 U.S.C. 154(b) by 335 days.

(21) Appl. No.: 10/504,599

(22) PCT Filed: Sep. 26, 2002

(86) PCT No.: PCT/JP02/09983

§ 371 (c)(1),
(2), (4) Date: Aug. 16, 2004

(87) PCT Pub. No.: WO03/068989

PCT Pub. Date: Aug. 21, 2003

(65) Prior Publication Data

US 2005/0272033 A1    Dec. 8, 2005

(30) Foreign Application Priority Data

Feb. 15, 2002 (JP) .............................. 2002-039040
Mar. 29, 2002 (JP) .............................. 2002-132119

(51) Int. Cl.
*C12Q 1/68* (2006.01)
*C12P 19/34* (2006.01)
*C07H 21/04* (2006.01)

(52) U.S. Cl. ...................... 435/6; 435/91.1; 435/91.2; 536/23.1; 536/24.3

(58) Field of Classification Search ........................ None
See application file for complete search history.

(56) References Cited

FOREIGN PATENT DOCUMENTS

WO    WO 98/04737    2/1998

OTHER PUBLICATIONS

Bryan et al., 1998, J. of Cereal Science, 28: 135-145.*
Buck et al., Biotechniques (1999) 27(3):528-536.*
Jiang et al., "New 18S 26S ribosomal RNA gene loci: chromosomal landmarks for the evolution of polyploid wheats", Chromosoma, vol. 103, Jan. 13, 1994, pp. 179-185, XP008072808.
Ann Briney et al., "A PCR-based marker for selection of starch and potential noodle quality in wheat", Molecular Breeding, vol. 4, 1998, pp. 427-433, XP008051617.
K.R. Gale et al., "Application of a high-throughput antibody-based assay for identification of the granule-bound starch synthase *Wx-Blb* allele in Australian wheat lines", Australian Journal of Agricultural Research, vol. 52, 2001, pp. 1417-1423, XP008051614.
Maruyama, N. et al. "Identification of major wheat allergens by means of the *Escherichia coli* expression system" European Journal of Biochemistry, Berlin, DE, vol. 255, No. 3, Aug. 1, 1998, pp. 739-745 XP002188677.
Allmann M. et al., Polymerase chain reaction (PCR): a possible alternative to immunochemical methods assuring safety and quality of food. Detection of wheat contamination in non-wheat food products, Z Lebensm Unters Forsch, 1993, vol. 196, No. 3, pp. 248 to 251.
Allmann M. et al., Detection of Wheat contamination in dietary non-wheat products by PCR, Lancet, 1992, vol. 339 No. 8788, p. 309.
Singh N.K. et al., Isolation and characterization of wheat triticin cDNA revealing a unique lysine-rich repetitive domain, Plant Mol Biol, 1993, vol. 22, No. 2, pp. 227 to 237.
Subramaniam K. et al., Isolation of a zeta class wheat glutathione S-transferase gene, Biochim Biophys Acta, 1999, vol. 1447, Nos. 2 to 3, pp. 348 to 356.
Murai, J. et al., Isolation and characterization of the three Waxy genes encoding the granule-bound starch synthase in hexaploid wheat, Gene, 1999, vol. 234, No. 1, pp. 71 to 79.

* cited by examiner

*Primary Examiner*—Sarae Bausch
(74) *Attorney, Agent, or Firm*—Young & Thompson

(57) ABSTRACT

A method of testing the presence/absence of wheat in a food by performing PCR with the use of primers which have been designed on the basis of data obtained from a part of a gene of wheat. This method is highly useful in detecting a trace component contained in a food or identifying a harmful allergen of wheat.

6 Claims, 5 Drawing Sheets

SEQUENCE LISTING

<160> NUMBER OF SEQ ID NOS: 15

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catcacaatc aacttatggt gg                                                  22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttgggagtt gagacgggtt a                                                   21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtggttgga atggtttaga gg                                                  22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttgggagttg agacgggtta tc                                                  22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgtgtattt tcttggtccc ga                                                  22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aggctacaca aacaatacag cc                                          22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgctctcacc ctacaactca g                                           21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctgaaggtg catctggctg                                             20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctgtgtatt ttcttggtcc cg                                          22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggctacacaa acaatacagc cc                                          22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgacgtgaa gaaggtggtg                                             20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

-continued

```
gcatcctaaa ccagaccaga g                                              21

<210> SEQ ID NO 13
<211> LENGTH: 1567
<212> TYPE: DNA
<213> ORGANISM: Triticum aestivum

<400> SEQUENCE: 13 tcctttttt  atgaaacaca  atggaccttt  gttgatatct  ctctcctcct  caaacagtta     60
tggcagctac  tagtttcgct  tcgctctctt  tttacttctg  cattttgctc  ttgtgccata    120
gctccatggc  acaactgttt  ggcatgagct  ttaacccatg  gcaaagctct  caccaagggg    180
gtttcagaga  gtgtacattc  aataggctac  aagcatctac  accacttcgt  caagtgaggt    240
cacaagcagg  cctgaccgag  tatttttgatg  aggaaaatga  acaatttcgt  tgtactggtg    300
tatttgccat  ccgtcgtgta  atcgaacctc  gtggttattt  gttaccgcga  taccacaaca    360
ctcatggatt  agtctacatc  atccaaggaa  gtggtttcgc  cggactgtct  tttcctggat    420
gcccagagac  attccagaaa  cagtttcaaa  atatgggca   atcacaatcc  gtacagggtc    480
aaagccaaag  ccaaaagttt  aaagatgagc  accaaaaagt  tcaccgtttc  agacaaggag    540
atgtcattgc  attaccggca  ggaattgtac  attggttcta  caatgacggt  gatgcgccaa    600
ttgtggctat  ctatgtttc   gacgtaaaca  actatgctaa  tcaacttgag  cctaggcata    660
aggaattttt  gttcgctggc  aactatagga  gttcgcaact  tcactctagt  caaaacatat    720
tcagtggttt  cgatgttcga  ttgcttgctg  aggccttggg  tacaagtgga  aaaatagcgc    780
aaaggcttca  aagtcaaaat  gatgacataa  ttcatgtgaa  tcatacccttt aaatttctga    840 agcctgttt   tacacaacag  cgagacgcag  aatcccgcac  actcaatatg  aggaagggca    900
atctcaggca  aaacactctc  aggaagagca  acctcaaatg  gggcagtcac  aggaagagca    960
acctcaaatg  gggcagtcac  agggagagca  gcctcaaatg  gggcagtctc  aggcaaagca   1020
ctcagggaga  gcaacctcaa  atggggtggt  ctcaggcaaa  gcactctcag  ggagaccagc   1080
ctgaagaagg  gcagggaggg  caatctcaac  aagaacaatc  tcaggcaggg  ccatatccgg   1140
gatgtcaacc  tcatgcaggg  cgatctcatg  catcacaatc  aacttatggt  ggttggaatg   1200
gtttagagga  gaactttgt   gatcataagc  taagtgtgaa  catcgacgat  cccagtcgtg   1260
ctgacatata  caatccgcgt  gccggtacga  taacccgtct  caactcccaa  acgttcccca   1320
tccttaacat  cgtgcaaatg  agtgctacaa  gagtacatct  ctaccagaac  gccattattt   1380
caccattatg  gaacattaat  gcccatagtg  tgatgtacat  gatccaagga  catatctggg   1440
ttcaggttgt  caatgaccat  ggtcgaaatg  tgttcaatga  ccttattagt  ccggggcaac   1500
tattaatcat  accacagaac  tatgttgttc  tgaagaaggc  acaacgtgat  ggaagcaagt   1560
acattga                                                                1567

<210> SEQ ID NO 14
<211> LENGTH: 2947
<212> TYPE: DNA
<213> ORGANISM: Triticum aestivum

<400> SEQUENCE: 14
ggggtagcag  tcagccatgg  cgacggccaa  gcccatcctg  tacggcgcct  ggatcagctc     60
ttgctctcac  cgtgtccgga  tcgctctcaa  cctcaaaggt  gagtagtact  tgttgaggtt    120
ttggagcttc  aatcgcttcg  gttcggttct  tcttgattat  gttaaccccc  agattagttt    180
atactcagct  tctccatccc  tatggtccta  gacctagagt  tgattatgtt  tatgctaggt    240
```

```
tcataacact cttcagttgg gaacatttca gatgccacca gctgtgtatt ttcttggtcc    300
cgaacatgta tatgactatc ataattaaga atattgttgt tcttttagct tttgccttgt    360
ttctttctt cagttcttct ctgttttcgt ttttggtttt ccctttgttt tagtttgggc     420
tgtattgttt gtgtagcctc ggcaccttgt tgtagtacaa aatgacgcac acttaggtgc    480
gtgttcaaga aaatgatta atgcagcaaa ttagatgtat taagaatttc ggtgcacaat     540
taaacgatat aagttttagg gtcttgttca ggaaactaat taatttatta tatgtgatgt    600
aggtgtggac tatgagtata aggcagtcaa tcctcggaca gatccaggta ctcaaattta    660
ccagataaca tgcccgtata ctaattataa agccatctga tccccgtttt tttaaacaaa    720
acatctcatt tccggtttgc aattgatgag agctcaaaat ggcaactgtc agagttgatg    780
tgatgaatga aatatgatcg tgttcagttt acatgtaaaa tgtgatagat gttgcctcat    840
gatgcctact tatgccttat tactaggcta gtagccgcct aatttgcagg gaactgcgca    900
tagactattc cttccctgga cattagctta gtctgctata acaactttgt gcaccatctt    960
tgatgatgaa atcttggct tgatcaatga tacaattgca atgcatattg tacccatcta   1020
ttcccaatgc tgaaatctac ggaatgttga aaaacgcata atttgtattc tgttttagga   1080
gaattcaccg ttatggattt cttattgcag actatgaaaa aataaacccg atcaaataca   1140
taccagcatt ggtagatggg gactttgttc tatctgattc tctcgctatc atgttggtga   1200
gtcacaattc ttgcttcagt ggattaagaa tgtgttttt cagcattcct gtccctctgt    1260
tattagttaa caagtgtttt ttttttgcac tgagcagtat ctggaggata agtatcctca   1320
gcatcctctc gtacctaaag atatcaaaac gaaaggtctt gatcttcagg tatatgtccg   1380
gctcaagatt ttctttagtt atttttcta gaaaatctc ttctatagtt ctatttctgt     1440
atcttgttaa tcacatgaac catagttgtt cagcactctt ttccgaacca tagttattca   1500
gcacacttat cggtaactcc atatggacta gctaattaca ttatttgctt gttgcagatt   1560
gcgaacatag tttgctcaag catccaacct ctccaaggct acggcgtaat tgtgggtttt   1620
tccgggagtt agctaccgct gacaagattt cgtcttctca atgatcatac gagtacgagt   1680
ttgatagcgt gtgtgtgcaa tatttgttta cttgcaggg tttacatgag ggtaggttga    1740
gccccgatga gagccttgag gtggttcaac gttatattga caagggcttc agaggtgcga   1800
tatttcgcaa catactgtct gcacagttac ataccgtcat atttgagaga aggggaattc   1860
agaatctctt ttttgtcttc tagactttcc tttttctcaga cattcttcca tcatatgcga   1920
cagagatatg ttcagttgtg ctgtcctgag ttctgacccc catcaaccat gcttattatt   1980
tgttcagttg accaaaacaa tcttactctt ggtctgctct tattatctgt tgcagcaatc   2040
gaaaagcttt tggatggatg tgacagcaaa tattgcgttg gagatgaagt ccatttggtt   2100
tgtgtttctg aacctacaca cttcttcact gatacatgtt tgatgctttg ccttgatcag   2160
tcaccttgaa atgaacttcc aattcaacat gatcaaattg attccggact cccaatttcc   2220
ttaattagca tgtcactatt attactaaat gtgctagtac ttactaatct tgagctatat   2280
attgtgatac atgtacattc gtggccttgg cagggagatg tgtgtctagc cccacagatc   2340
catgccgcca tcaatcgctt ccagattgat atggtactca ctttctctct gatattctct   2400
gtgcaaatta agatttctgc tgctctcacc ctacaactca gaaatccaat agcaacaagc   2460
tttcctttc ttacagacga agtacccaat attgtcgcga cttcacgacg catacatgaa    2520
aattccggca tttcaagctg cactgcccca gaatcagcca gatgcacctt cagcaaaata   2580
```

| | |
|---|---:|
| atcaagaaat caagccagtt acaactacat gcgtgtaatt tacgcaataa tgaggaatgt | 2640 |
| agtagtctgc aattgaagaa cctctcataa gtcataactt gttccctccg tccaggtgca | 2700 |
| tagggcatct aatgaaaatt tagtattcca aatatataag tcaccatgcg tggaagaagc | 2760 |
| ccctctacat gccatgccga gctgccggcc gggctccggc accatgtaaa ttaatattta | 2820 |
| tcgattcacc accagtgaga ttcagcagaa aaaaaaggtg atttgacgaa ttgacctgta | 2880 |
| tctataaccg attttctctc ttggatttgt atttactgct ggatattttt tgcggggat | 2940 |
| ttattgg | 2947 |

```
<210> SEQ ID NO 15
<211> LENGTH: 2886
<212> TYPE: DNA
<213> ORGANISM: Triticum aestivum

<400> SEQUENCE: 15
```

| | |
|---|---:|
| cctgcgcgcg ccatggcggc tctggtcacg tcccagctcg ccacctccgg caccgtcctc | 60 |
| ggcatcaccg acaggttccg gcgtgcaggt ttccagggcg tgaggccccg gagcccggcg | 120 |
| gatgcggctc tcggcatgag gaccgtcgga gctagcgccg ccccaacgca aagccggaaa | 180 |
| gcgcaccgcg ggacccggcg gtgcctctcc atggtggtgc gcgccaccgg cagcggcggc | 240 |
| atgaacctcg tgttcgtcgg cgccgagatg gcgccctgga gcaagaccgg cggcctcggc | 300 |
| gacgtcctcg ggggcctccc cccagccatg gccgtaagct agacagcacc actgtcttct | 360 |
| cataatgttc atcttgcagt tgcagccatg cctgccgtta caacgggtgg tgtgtccgtg | 420 |
| caggccaacg gccaccgggt catggtcatc tccccgcgct acgaccagta caaggacgcc | 480 |
| tgggacacca gcgtcgtctc cgaggtactt gaaccctacc cgcaactta acgatcaaaa | 540 |
| ttcgcatgct cctgcacatt tctgcaggat cctactgact gactaactgg atctcgcaga | 600 |
| tcaaggtcgt tgacaagtac gagagggtga ggtacttcca ctgctacaag cgcggggtgg | 660 |
| accgcgtgtt cgtcgaccac ccgtgcttcc tggagaaggt gaccgatcgt cgtcgtggac | 720 |
| cgatcaagct agctcttcgt cgtctcaacc ttgataggca tggtgattga tttcagttgt | 780 |
| ttctgctggt tgcaatttcc aggtccgggg caagaccaag gagaagatct acgggcccga | 840 |
| cgccggcacg gactacgagg acaaccagca gcgcttcagc cttctctgcc aggcggcgct | 900 |
| ggaagtgccg aggatcctga acctcgacaa taaccctac ttttctgggc cctacggtaa | 960 |
| gatcaagatc aagcacgcct actagttcaa gctagagtgt gtgtaatctg aactctgaag | 1020 |
| aacttgatat tttcttgaga gagctggatg atcaccattt ttttttgtat ctgggtgccg | 1080 |
| tcgtcgtccc ttgttgcgcg ccgcgcaggg gaggacgtgg tgttcgtgtg caatgactgg | 1140 |
| cacacgggcc ttctggcctg ctacctcaag agcaactacc agtccaatgg catctacagg | 1200 |
| gccgcaaagg ttttgcatct tcttctcaaa ctatatatcc tctctgcatt catatgcatg | 1260 |
| catatcttgc tcttcattct gaaacaggca tatcaattt gcggttcatt ctggcctgaa | 1320 |
| ttttacattg caacttcatt tcatggccag gtggcattct gcatccacaa catctcgtac | 1380 |
| cagggccgct tctccttcga cgacttcgcg cagctcaacc tgcccgacag gttcaagtcg | 1440 |
| tccttcgact tcatcgacgg ctacgacaag ccggtggagg ggcgcaagat caactggatg | 1500 |
| aaggccggga tcctgcaggc cgacaaggtg ctgacggtga gccctacta gcggaggag | 1560 |
| ctcatctctg gcgaagccag gggctgcgag ctcgacaaca tcatgcgcct cactgggatc | 1620 |
| accggcatcg tcaacggcat ggatgttagc gagtgggacc ccaccaagga caagttcctc | 1680 |
| gccgtcaact acgacatcac caccgtgagc aaccacacaa agatttcttc ctcttcttcc | 1740 |

```
ggtgatcgct ggttctgggt gggttctcac gaacgaggca aagtgacagg cgttggaggg    1800
gaaggcgctg aacaaggagg cgctgcaggc cgaggtgggg ctgccggtgg accggaaggt    1860 gccctggtg gcgttcatcg gcaggctgga ggagcagaag ggccccgacg tgatgatcgc    1920
cgccatcccg gagatcctga aggaggagga cgtccagatc gttctcctgg tacatcatcg    1980
agcccgcaac ccgaccgcca ttgctgaaac ttcgatcaag cagacctaag gaatgatcga    2040
atgcattgca gggcaccggg aagaagaagt tcgagcggct actcaagagc attgaggaga    2100
aattcccgag caaggtgagg gccgtggtca ggttcaacgc gccgctggct caccagatga    2160
tggccggcgc cgacgtgctc gccgtcacca gccgcttcga gccctgcggc ctcatccagc    2220
tccaggggat gcgctacgga acggtaaact tttccttctt gccaagtcct tacttcctga    2280
gcaatcatga gccatgccca tgaccgaagt ttcttccaaa ttttcagccg tgcgcgtgcg    2340
cgtccaccgg cgggcttgtc gacacgatcg tggagggcaa gaccgggttc cacatgggcc    2400
ggctcagtgt cgatgtaagt tcatcaatct cttcaataaa ttcttcatct tgttcatcct    2460
gggagctcag gcagatcatc aaacgggttt ccttttcct cttggtggcc agtgcaacgt    2520
ggtggagccg gccgacgtga agaaggtggt gaccaccctg aagcgcgccg tcaaggtcgt    2580
cggcacgccg gcataccatg agatggtcaa gaactgcatg atacaggatc tctcctggaa    2640
ggtaagtcag tctctggtct ggtttaggat gcattttcca gaacaactaa gagttaagac    2700
tacaatggtg ctcttgttcg atgtatccat taatggtggc ttgcgcatat ggtgcagggg    2760
ccagccaaga actgggagga cgtgcttctg gaactgggtg tcgaggggag cgagccgggg    2820
gtcatcggcg aggagattgc gccgctcgcc atggagaacg tcgccgctcc ctgaagagag    2880
aaagaa                                                               2886
```

METHOD OF TESTING WHEAT

TECHNICAL FILED

The present invention relates to a wheat detecting method, and more specifically to a method for detecting presence of wheat contained in a food in a trace amount over the entire distribution stage in order to indicate the presence/absence of wheat as an allergic substance in the food.

BACKGROUND ART

Recently, to prevent health hazard attributed to foods containing allergic substances, requests for information service by indication thereof have increased. The indication of foods containing allergic substances has been made obligatory with enforcement of amendments to the Statutes on the Food Sanitation Law in April, 2001. In particular, with respect to five items (specified raw materials) of eggs, milk, and wheat which cause allergy most often, and buckwheat and peanuts which cause serious symptoms, it has been made obligatory to perform proper indication over the entire distribution stage.

There are individual differences as to what food people recognize as an allergen as the allergic substance. Thus, if a specified substance contained in the food is properly indicated even when the specified substance is contained in a trace amount, a person who ingests the food can know the presence/absence of the allergen contained in the food, so that health hazard can be prevented. However, it has been difficult to detect the presence/absence of a trace amount of a specified substance in a food having been heated or otherwise processed, by conventionally known methods for food analysis.

In addition, when a specified raw material is used by a producer in his or her company, it is a matter of course that the specified raw material can be indicated on processed foods. However, when a specified raw material is used as an intermediate material of a final product, it is hard in some cases to confirm the presence/absence of the specified raw material contained in a trace amount, particularly in a purchased intermediate material. Unintended inclusion may also actually occur.

Therefore, for food manufacturers, it is important to precisely comprehend food additives such as processing aids and carry-over remaining in trace amounts or actual states of mutual contamination between manufacturing lines, and take proper measures as well as provide consumers with correct information based on the laws. Therefore, it has been desired to provide a technology of precisely analyzing allergic substances.

In particular, wheat is very often used as a raw material of various food products, and in most cases, the use of wheat in final products cannot be determined only from the appearance of the food product. Moreover, allergic symptoms due to wheat are serious, the number of patients is prone to increase along with the diet westernization, and wheat is now one of the major substances causative of immediate allergy.

Thus, wheat is defined as one of the specified raw materials in the indication of foods containing allergic substances under the Food Sanitation Law, and it has been made obligatory to indicate the presence of wheat when the wheat is included in the food.

However, there has been also no proper measuring method to detect the wheat, and a reliable measuring method for a trace amount component has been desired.

An object of the invention is development of a method for measuring the presence/absence of wheat in a food based on the findings obtained from attempts to construct primers specific to wheat, to identify the detection limit by an analysis system thereof, and to apply the primers to processed foods for the purpose of developing a method for precisely analyzing the presence/absence of the wheat included in the food.

DISCLOSURE OF THE INVENTION

[1] The present invention relates to a method for measuring presence/absence of wheat in a food, including: designing primers based on genetic information obtained from a part of wheat genes; and performing PCR (Polymerase Chain Reaction).

[2] Further, the present invention relates to a method for measuring presence/absence of wheat for indicating the presence/absence of a trace amount component in the food, including: designing primers based on information obtained from a part of wheat genes; and performing PCR.

[3] The present invention also relates to a method for measuring presence/absence of wheat in a food, including: designing primers based on information obtained from a part of wheat genes; and performing PCR to discriminate the food containing an allergen of the wheat harmful for food ingesting person, a method for providing information as to whether the food contains wheat containing an allergen harmful for patients with food allergy or suspects thereof, or a method for indicating one of these about a food.

[4, 5] Here, the food may be a processed food or a food raw material. The foods include not only foods for human beings but also foods (feedstuff) for animals.

[6 to 8] Here, it is preferable that the gene and the primers be as follows:

(1) A wheat gene is shown in SEQ ID NO:13 and the primers include a sense primer and an anti-sense primer composed of at least 5 to 35 consecutive DNA fragments selected from information of a sequence from position 661 to position 1,320;

(2) the gene is a wheat gene shown in SEQ ID NO:14 and the primers include a sense primer and an anti-sense primer composed of at least 5 to 35 consecutive DNA fragments selected from information of a sequence from position 181 to position 540; or (3) the gene is a *Triticum aestivum* gene for starch synthase (GBSSI) (WX-D1), complete cds. (Accession #AB019624, full length: 2,886 bps) and the primers include a sense primer and an anti-sense primer composed of at least 5 to 35 consecutive DNA fragments selected from information of a sequence from position 2,401 to position 2,886.

The primers are complementary chains of a target gene, and sequence portions of N-terminus and C-terminus of the target gene are selected as a pair. Lengths in the pair may be the same or different.

[9] of the pairs of a sense and an anti-sense primer of (1) to (3) described above, primer pairs of Wtr 01 (SEQ ID NO:1)/Wtr 10 (SEQ ID NO:2), Wgs 05 (SEQ ID NO:5)/Wgs 10 (SEQ ID NO:6), and Wgs 11 (SEQ ID NO:9)/Wgs 12 (SEQ ID NO:10) shown in Table 3 are more preferable, and Wtr 01 (SEQ ID NO:1)/Wtr 10 (SEQ ID NO:2), and Wgs 11 (SEQ ID NO:9)/Wgs 12 (SEQ ID NO:10) are particularly preferable.

It is known that if PCR primers used for PCR are used for amplifying substantially in the same region of template DNA (the sequences of SEQ ID NOS:13 to 15 are illustrated), they have the same function and produce the same result (PCR product). In the case of wheat, for example the individual primer sequence has the same function even if it is shifted by several to over 10 nucleotides on the corresponding same template DNA sequence toward 5'-upstream side or 3'-downstream side.

Therefore, the preferable primer pairs are not limited to those in Table 3, and those which can substantially accomplish the same functions as those of the above primer pairs in Table 3 are also included in the preferable primer pairs.

For the above primers, the primer where one or several nucleotides are deleted, substituted, added, and/or inserted and which hybridizes to the corresponding region of the template DNA is substantially the same as the above primers. The preferable primers in the present invention for example, include the primers having sequence shifted by one to several nucleotides or over 10 nucleotides toward 5'-upstream/downstream side and/or 3'-upstream/downstream side on the corresponding template DNA sequence complementary to the sequence of the primers of SEQ ID NOS:1 to 12. The preferable primers also include at least 80%, more preferably 90% or more, and still more preferably 95% or more of consecutive sequence in SEQ ID NOS:1 to 12.

[10] Also, the present invention provides a method where a clear amplified band is given in analytes containing one or more species of wheat selected from the group of wheat described below but is not given in analytes containing animal and plant materials (food raw materials derived therefrom) except rye and wheat, on an electrophoresis of the analyte subjected to PCR using the primers.

Wheat group: strong wheat, mellow (mellower strong) wheat, weak wheat, durum (macaroni) wheat, and other edible single kernel wheat.

Specific examples of the wheat may include Western White (US), Canadian Spring Wheat No. 1 (Canada), Australian Standard Wheat (Australia), Norin 61 (Japan), and Canadian Amber Durum (durum wheat, Canada).

[11] There are provided PCR primers which are designed based on information obtained from a part of a wheat gene and a set of reagents (kit) containing the same for measuring presence/absence and/or a concentration of wheat in a food.

BRIEF DESCRIPTION OF THE DRAWINGS

FIG. 1 is an electrophorogram showing the specificity of the primers to wheat.

FIG. 2 is an electrophorogram showing detection limit of a wheat detection system using PCR.

BEST MODE FOR CARRYING OUT THE INVENTION

Figure 1A:
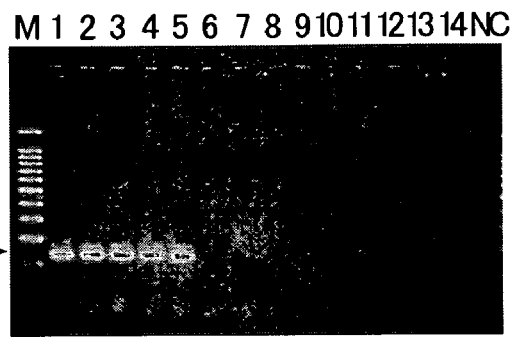
FIG. 1a shows the specificity of the primers, Wtr 01/10 to wheat.
Figure 1B:
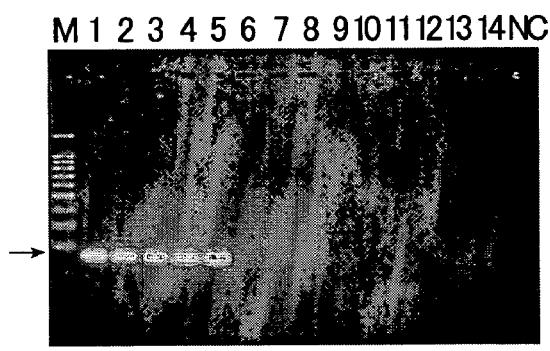
FIG. 1b shows the specificity of the primers, Wgs 11/12 to wheat.
Figure 1C:
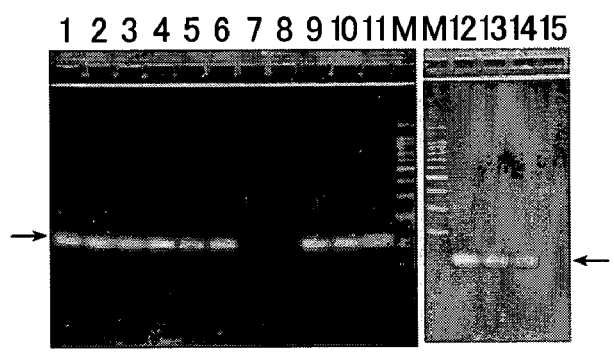
FIG. 1c shows the results of the specificity of the primers, Wtr 05/06 to wheat.
Figure 1D:
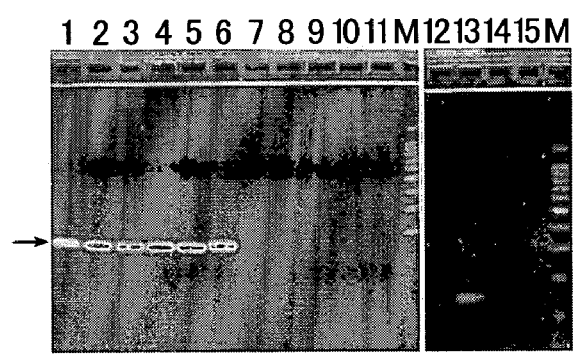
FIG. 1d shows the specificity of the primers, Wgs 07/08 to wheat.
Figure 1E:
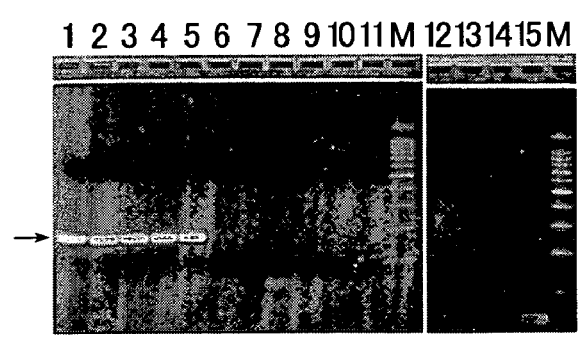
FIG. 1e shows the results of the specificity of the primers, Wgs 05/10 to wheat.

The invention is more specifically illustrated.

The invention is a method for measuring the presence/absence of wheat in foods, comprising designing primers based on information obtained from a part of a gene of the wheat and performing PCR.

The foods measured as subjects may be raw materials, materials in any step of processing, or foods after the processing. The method of the invention can detect the presence/absence of wheat or wheat DNA a trace amount of preferably 0.1% or less, 1000 ppm or less, further 500 ppm or less, and 100 ppm or less by weight ratio in food. With this method, if a wheat gene is contained in a food, the presence/absence of wheat can be detected even when wheat which is not intended by a producer is present in a trace amount as a part of seasoning or an additive. Genes are relatively stable by food processing such as heating compared to other substances derived from organisms such as proteins, and the presence in a trace amount can be detected in a food heated, cooked or otherwise processed.

A nucleotide sequence of a wheat gene may be determined by any known methods when the sequence is unknown, but nowadays numerous known gene information can be used. For example, the information of the whole sequence of each of wheat genes is obtained from the database at National Institute of Genetics (DDBJ) and the like, and a pair (set) of a sense primer and an anti-sense primer suitable for PCR can be selected and designed based on a part of the sequence.

In the design of the primers, attention was paid to the following items considering the testing method of the invention. (i) A GC content in a primer is from 40 to 60%; (2) A melting temperature ($T_m$ value, see below) of a primer is from 55° C. to 70° C.; (iii) $T_m$ values of two primers in the pair are close to each other; (iv) Two primers have no complementary sequences at 3' terminus; (v) The primer itself forms no high order structure such as hairpin; (vi) A full length of the primer is 15- to 35-mers; (vii) A GC content at 3' terminus of the primer is reduced; (viii) A sequence where the same nucleotide is consecutive in large numbers in the primer is avoided; (ix) The sequence of the primer is not necessary to be completely complementarily identical to that of the template DNA but complementarity at 3' terminus is increased; (x) There is no additional sequence complementarily identical to that of the primer in a template DNA used except at a primer portion.

The primers of the invention are required to be usable for not only wheat as a raw material but also foods during and after the processing such as heating and cooking. Further, it is considered that the template DNA of wheat is not intact but is fragmented. (xi) A region of the gene amplified by the two primers is preferably relatively short. Moreover, it is necessary to design primers which fulfill all of the conditions of (i) to (xi) in one region of a gene that is commonly conserved in various species of wheat. However, it is very difficult to prepare primers which fulfill all of those conditions from DNA sequence composed of only four nucleotides, A, C, G, and T. Therefore, the design of the primers is a quite difficult problem when PCR is performed. Also, even if the primer that fulfills those many conditions can be designed, that is only a necessary condition for performing PCR. It is unknown whether the intended PCR is successful unless the PCR is actually performed.

A PCR method is not particularly limited and includes various known improved methods. In one example, a pair of primers and a template (analyte) DNA are mixed with reagents such as Tris-HCl, KCl, MgCl$_2$, dNTPs, and Taq DNA polymerase to give a reaction solution for the PCR. One cycle of the PCR is composed of three steps: heat denaturation, annealing of the primers, and a DNA synthetic reaction by DNA polymerase. The respective steps require different or, in some cases the same reaction temperatures and times, and thus, proper ranges are determined depending on the nucleotide sequence and length of the DNA region to be amplified. A thermal cycler is commercially available for such manipulations. The following formula obtained from the GC content and the length of the sequence:

$$Tm(°C.)=4\times(G+C)+2\times(A+T)$$

is an indicator of the annealing temperature. The size of PCR product is adjusted to 50-500 bp, preferably about 100-150 bp. Within this range, DNAs fragmented in the processed food can be detected.

In the present invention, the gene and the primers are preferably as follows:

(1) the wheat gene is shown in SEQ ID NO:13 and the primers include a sense or anti-sense primer which is composed of at least 5 to 35 consecutive DNA fragments selected from a sequence from position 661 to position 1,320;

(2) the wheat gene is shown in SEQ ID NO:14 and the primers include a sense or anti-sense primer which is composed of at least 5 to 35 consecutive DNA fragments selected from a sequence from position 181 to position 540; or (3) the wheat gene is shown in SEQ ID NO:15 and the primers include a sense or anti-sense primer which is composed of at least 5 to 35 consecutive DNA fragments selected from a sequence from position 2,401 to position 2,886.

Among the pairs of sense and anti-sense primers of (1) to (3) described above, preferable primer pairs are Wtr 01 (SEQ ID NO:1)/Wtr 10 (SEQ ID NO:2), Wgs 05 (SEQ ID NO:5)/Wgs 10 (SEQ ID NO:6), and Wgs 11 (SEQ ID NO:9)/Wgs 12 (SEQ ID NO:10) shown in Table 3, and particularly preferably Wtr 01 (SEQ ID NO:1)/Wtr 10 (SEQ ID NO:2), and Wgs 11 (SEQ ID NO:9)/Wgs 12 (SEQ ID NO:10).

The primers are complementary chains of a target gene, and portions of N-terminus and C-terminus of the target gene are selected. Lengths in the pair may be the same or different.

As described below in "identification of specificity", even when the primers in the pair [Wtr 05 (SEQ ID NO:3)/Wtr 06 (SEQ ID NO:4), Wgs 07 (SEQ ID NO:7)/Wgs 08 (SEQ ID NO:8)] have the same T$_m$ value, they are sometimes inappropriate for the detection, and thus, selection of the primers is important.

When suitable PCR conditions such as concentrations of Taq DNA polymerase and MgCl$_2$, and the reaction cycle number are examined or nested PCR is used, there is a possibility that detection sensitivity is further increased.

A PCR product may be identified using an immune reaction or by any other method. When a clear band is observed on an electrophorogram (electrophoresis pattern) by performing electrophoresis using positive and negative controls if necessary, the presence of a detection substance (wheat) in an analyte (food) can be confirmed.

The method of the present invention is effective when the wheat as a detection substance is contained in the analyte (food).

The term "wheat" as used herein refers to strong wheat, mellow (mellower strong) wheat, weak wheat, durum (macaroni) wheat, and other edible single kernel wheat.

Specific examples of the wheat include Western White (US), Canadian Spring Wheat No. 1 (Canada), Australian Standard Wheat (Australia), Norin 61 (Japan), and Canadian Amber Durum (durum wheat, Canada).

The method of the invention can be easily conducted by using a set of reagents (kit) containing the primers designed based on the information obtained from a part of the wheat gene. The set of the reagents (kit) may contain known reagents conventionally used for PCR, or may be equipped with another apparatus such as an electrophoresis apparatus. The reagents include dNTPs, MgCl$_2$, Taq polymerase, Tris-HCl, glycerol, DMSO, DNA for positive control, DNA for negative control, and distilled water. Those reagents may be provided in an individually packed state or in a form where two or more reagents in the kit are mixed with each other. Concentrations of respective reagents in the kit are not particularly limited, and may be in the ranges suitable for the PCR of the invention. Also, the kit may include information on suitable PCR conditions or the like, or may be only composed of the primer reagents.

DNAs are stable to heat and can be detected in trace amounts in processed foods. Therefore, the obtained result can be utilized for indication on foods or as information on food allergies. In addition, by detecting wheat in the food, it is possible to detect a trace amount of wheat remaining in food additives such as processing aids and carry-over or presence of wheat which is not intended by a producer such as mutual contamination between manufacturing lines.

Hereinafter, the present invention is concretely illustrated, but the invention is not limited thereto.

(1) Construction of Primers for Detection of Wheat

Before constructing primers for the detection of DNA derived from wheat, the inventors accessed the database in the National Institute of Genetics (DDBJ), searched for known genes of wheat (*Triticum aestivum*), and selected genetic information concerning the following wheat reserve proteins: (1) *Triticum aestivum* triticin precursor, mRNA, partial cds. (Accession #S62630, full length: 1,567 bps) (SEQ ID NO:13), (2) *Triticum aestivum* glutathone S-transferase (GST) gene, complete cds. (Accession #AF109714, full length: 2,947 bps) (SEQ ID NO:14), and (3) *Triticum aestivum* gene for starch synthase (GBSSI) (Wx-D1), complete cds. (Accession #AB019624, full length: 2,886 bps) (SEQ ID NO:15).

Next, it was confirmed by the BLAST search in DDBJ that there is no similar sequence to the sequence of the selected wheat gene in plants other than wheat.

In order to design the primer, the inventors searched for sequences which are candidates of the primers for a specific sequence of the wheat gene using software "GENETYX MAC". GENETYX MAC used can set up various conditions for primer design, e.g., (i) GC content and (ii) range of T$_m$ value which were difficult to determine by manual calculation. As a result, sequences of 126 pairs of the candidate primers were found. The inventors have uniquely searched for the sequences which fulfill all of the above conditions (i) to (xi) for the primer design and selected 12 pairs of primer sequences usable in the method of the invention. For the primer design in the method of the invention, the size of PCR amplified product was adjusted to about 100 to 150 bp in consideration of detection from fragmented DNA in processed foods. The thus selected 12 pairs of oligonucleotide primers (synthesized by Biologica Co.) were prepared.

(2) Extraction of DNA

Surfaces of seeds of wheat and other plants were washed with 1% Triton X (Wako Pure Chemical Industries Ltd.), rinsed with distilled water, dried well, and then the seeds were finely ground with Multi Bead Shocker (Yasui Kikai Co., Ltd.). Next, DNA was extracted from 1 to 1.5 g of a ground sample using Dneasy Plant Maxi kit (Qiagen). Powder samples such as flour were also finely ground, and then DNA was extracted using Dneasy Plant Maxi kit as the same manner as the above seeds. For processed foods, those whose water content was high were lyophilized for 24 hours, and those whose water content was low were directly used. Then, DNA was extracted from 1 g of each by using Genomic Tip 20/G (Qiagen). The concentration of the extracted DNA was determined by measuring the absorbance, and subsequently the DNA was diluted with purified water to 10 ng/μl and was used as a template (test) DNA sample of PCR.

(3) Detection of Wheat by PCR and Electrophorogram

A reaction solution of PCR was prepared as follows. 2.5 μl of a DNA sample solution adjusted to 10 ng/μl was added to a solution containing PCR buffer (PCR buffer II, Applied Biosystems), 200 μmol/L of dNTP, 1.5 mmol/L of $MgCl_2$, 0.5 μmol/L of 5' and 3' primers, and 0.625 unit of Taq DNA polymerase (AmpliTaq, Gold, Applied Biosystems) to obtain a total volume of 25 μl. Those with no description of a template DNA amount in Table 4 have this concentration. But, when the concentration of the extracted DNA was 10 ng/μl or less, when the absorbance $OD_{260}/OD_{280}$ of the DNA obtained from processed foods or the like containing many additives was 1.7 or less, the DNA was containing many impurities. When the purity of the DNA was low, 2.5 μl to 17.8 μl of the undiluted DNA solution or 10 ng/μl diluted solution was added to the PCR solution, and the total volume was adjusted to 25 μl with purified water. Those with the description of the template DNA amount in Table 4 have this concentration.

GeneAmp PCR System 9600 (Applied Biosystems) was used as a PCR amplification apparatus, and reaction conditions were set as follows. First, the temperature was retained at 95° C. for 10 min, and the reaction was started. Next, 95° C. for 30 sec, 60° C. for 30 sec, and 72° C. for 30 sec were set as one cycle, and 40 cycles of PCR were performed. Finally, a termination reaction at 72° C. for 7 min was conducted, and subsequently the solution was stored at 4° C. to give a PCR product solution.

The PCR product solution was subjected to electrophoresis using 2% agarose gel (2% E-Gel, Invitrogen) containing ethidium bromide. Validity of the PCR was determined by the presence/absence of an amplified band from a positive control (DNA extracted from the wheat seeds) and a negative control (blank reaction solution without template DNA). Then, the presence/absence of wheat in the sample was determined by identifying a DNA amplified band with optimal size produced by each set of primers.

(4) Experiment 1. Confirmation of Specificity of Primers for Wheat Detection

For the purpose of selecting primers for specific detection of wheat, PCR was performed using DNAs extracted from seeds of wheat and other plants. As samples of wheat, 5 species of wheat brands or cultivars [Western White (US), Canadian Spring Wheat No. 1 (Canada), Australian Standard Wheat (Australia), Norin 61 (Japan), and Canadian Amber Durum (Durum Wheat, Canada)] were used. Further, seeds of rye (Canada), barley (Minorimugi), oat (feedstuff for racehorse), rice (Koshihikari), maize (non GMO for feedstuff), soybean (Murayutaka), foxtail millet (Kumamoto), and rapeseed (Canola) and buckwheat were used as the other plants.

After the PCR, electrophoresis was performed, and primers which afforded a clear amplified band with optimal size only in the wheat samples but not in the other samples were selected as the primers which can specifically detect wheat.

FIG. 1a, FIG. 1b, FIG. 1c, FIG. 1d, FIG. 1e, and FIG. 5 respectively are electrophorograms showing the specificity of primers for detecting wheat: Wtr 01 (SEQ ID NO:1)/Wtr 10 (SEQ ID NO:2), Wgs 11 (SEQ ID NO:9)/Wgs 12 (SEQ ID NO:10), Wtr 05 (SEQ ID NO:3)/Wtr 06 (SEQ ID NO:4), Wgs 07 (SEQ ID NO:7)/Wgs 08 (SEQ ID NO:8), Wgs 05 (SEQ ID NO:5)/Wgs 10 (SEQ ID NO:6), and Wss 01 (SEQ ID NO:11)/ Wss 02 (SEQ ID NO:12).

Figure 5:
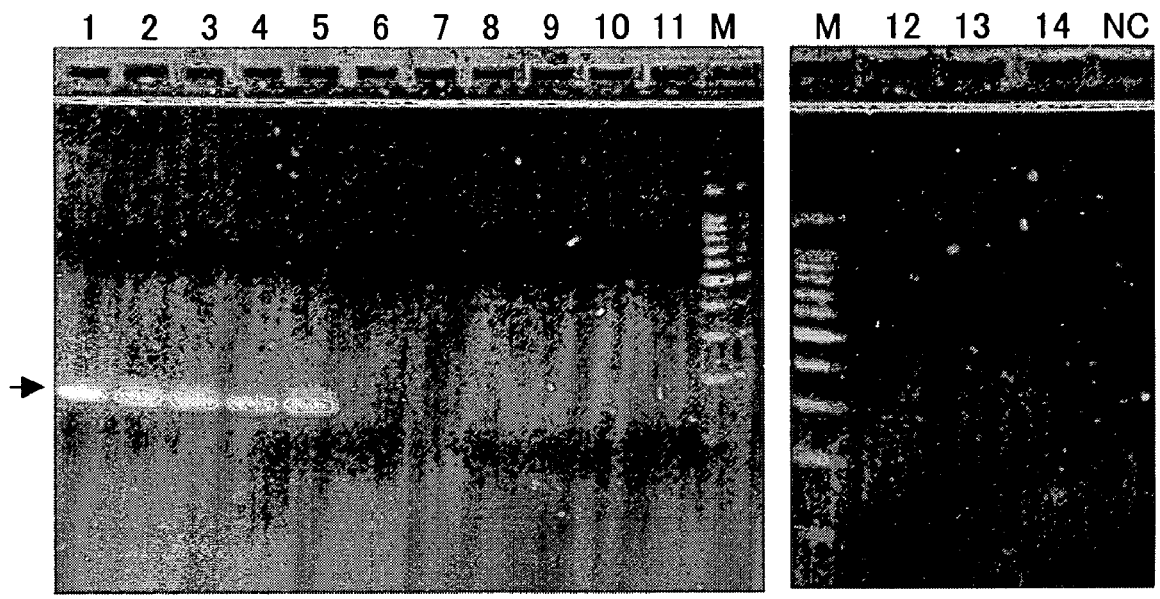
FIG. 5 is an electrophorogram showing the specificity of the primers, Wss 01/Wss 02 to wheat.

In FIGS. 1 and 5, M represents 100 bp ladder and NC represents no template control (blank without template DNA). Lane numbers (sample numbers) and results in FIG. 1 are shown in Table 1. Lane numbers (sample numbers) and results in FIG. 5 are shown in Table 2.

TABLE 1

| Lane numbers in FIG. 1 | Species | Brand or cultivar | Detection by PCR | | | | |
|---|---|---|---|---|---|---|---|
| | | | Wtr01/10 | Wgs11/12 | Wgs05/10 | Wtr05/06 | Wgs07/08 |
| 1 | Wheat | Western White | + | + | + | + | + |
| 2 | Wheat | Canadian Spring Wheat No. 1 | + | + | + | + | + |
| 3 | Wheat | Australian Standard Wheat | + | + | + | + | + |
| 4 | Wheat | Norin 61 | + | + | + | + | + |
| 5 | Wheat (durum) | Canadian Amber Durum | + | + | + | + | + |
| 6 | Rye | Canada | − | − | − | + | + |
| 7 | Barley | | − | − | − | − | − |
| 8 | Oat | Feedstuff for racehorses | − | − | − | − | − |
| 9 | Rice | Koshihikari | − | − | − | + | − |
| 10 | Maize | nonGMO | − | − | − | + | − |
| 11 | Soybean | Murayutaka | − | − | − | + | − |
| 12 | Foxtail millet | made in Kumamoto | − | − | − | + | − |

TABLE 1-continued

| Lane numbers in FIG. 1 | Species | Brand or cultivar | Detection by PCR | | | | |
|---|---|---|---|---|---|---|---|
| | | | Wtr01/10 | Wgs11/12 | Wgs05/10 | Wtr05/06 | Wgs07/08 |
| 13 | Rapeseed | Canola | − | − | − | + | − |
| 14 | Buckwheat | | − | − | − | + | − |
| 15, NC | No Template Control (Water) | | − | − | − | − | − |

TABLE 2

| Lane numbers in FIG. 5 | Species | Brand or cultivar | Detection by PCR Wss01/02 |
|---|---|---|---|
| 1 | Wheat | Western White | + |
| 2 | Wheat | Canadian Spring Wheat No. 1 | + |
| 3 | Wheat | Australian Standard Wheat | + |
| 4 | Wheat | Norin 61 | + |
| 5 | Wheat (durum) | Canadian Amber Durum | + |
| 6 | Rye | Canada | − |
| 7 | Barley | | − |
| 8 | Oat | Feedstuff for racehorses | − |
| 9 | Rice | Koshihikari | − |
| 10 | Maize | nonGMO | − |
| 11 | Soybean | Murayutaka | − |
| 12 | Foxtail millet | made in Kumamoto | − |
| 13 | Rapeseed | Canola | − |
| 14 | Buckwheat | | − |

As results of Experiment 1, three sets of primers, Wtr 01 (SEQ ID NO:1)/Wtr 10 (SEQ ID NO:2), Wgs 11 (SEQ ID NO:9)/Wgs 12(SEQ ID NO:10), and Wgs 05 (SEQ ID NO:5)/Wgs 10 (SEQ ID NO:6) are capable of specifically detecting wheat, and thus were selected as primers for detecting wheat from 10 pairs of primer candidates. In particular, sets of two primers, Wtr 01 (SEQ ID NO:1)/Wtr 10 (SEQ ID NO:2) and Wgs 11 (SEQ ID NO:9)/Wgs 12(SEQ ID NO:10) afford the clearest PCR amplified bands, and thus are preferably selected as the primers.

The set of primers, Wtr 05 (SEQ ID NO:3)/Wtr 06 (SEQ ID NO:4) was cross reacted with many kinds of grains in addition to wheat, and the set of primers, Wgs 07 (SEQ ID NO:7)/Wgs 08 (SEQ ID NO:8) was cross reacted with rye. The result shows that these sets of the primers are not appropriate for detecting wheat.

Furthermore, many other pairs of primers were cross reacted with rye which does not belong to the category of wheat defined as a specified raw material under the Food Sanitation Law.

Table 3 shows the above sets of primers.

TABLE 3

| Name | SEQ ID NO | Sequence | Tm | GC % | Position of primer START | END |
|---|---|---|---|---|---|---|
| sense Wtr01 | 1 | 5' CAT CAC AAT CAA CTT ATG GTG G 3' | 62 | 41 | 1,171 | 1,192 |
| anti-sense Wtr10 | 2 | 5' TTT GGG AGT TGA GAC GGG TTA 3' | 62 | 47 | 1,311 | 1,291 |
| sense Wtr05 | 3 | 5' GGT GGT TGG AAT GGT TTA GAG G 3' | 66 | 50 | 1,188 | 1,209 |
| anti-sense Wtr06 | 4 | 5' TTG GGA GTT GAG ACG GGT TAT C 3' | 66 | 50 | 1,310 | 1,289 |
| sense Wgs05 | 5 | 5' CTG TGT ATT TTC TTG GTC CCG A 3' | 64 | 45 | 282 | 303 |
| anti-sense Wgs10 | 6 | 5' AGG CTA CAC AAA CAA TAC AGC C 3' | 64 | 45 | 439 | 418 |
| sense Wgs07 | 7 | 5' TGC TCT CAC CCT ACA ACT CAG 3' | 64 | 52 | 2,421 | 2,441 |
| anti-sense Wgs08 | 8 | 5' GCT GAA GGT GCT TCT GGC TG 3' | 64 | 60 | 2,574 | 2,555 |
| sense Wgs11 | 9 | 5' GCT GTG TAT TTT CTT GGT CCC G 3' | 66 | 50 | 281 | 302 |
| anti-sense Wgs12 | 10 | 5' GGC TAC ACA AAC AAT ACA GCC C 3' | 66 | 50 | 438 | 417 |
| sense Wss01 | 11 | 5' CCG ACG TGA AGA AGG TGG TG 3' | 64 | 60 | 2,532 | 2,551 |
| anti-sense Wss02 | 12 | 5' GCA TCC TAA ACC AGA CCA GAG 3' | 64 | 52 | 2,672 | 2,652 |

(5-1) Experiment 2-1. Identification of Detection Limit of Wheat by PCR

In the experiment 2-1, for the purpose of examining the detection limit of wheat by PCR using the primers Wgs 11 (SEQ ID NO:9)/Wgs 12 (SEQ ID NO:10), artificially mixed samples of wheat were prepared at DNA level and powder level, and PCR was performed using solutions of the samples to identify the detection limit of wheat.

The artificially mixed samples at the DNA level were prepared by: diluting DNAs extracted from the seeds of wheat to 10 ng/μl; and mixing with salmon sperm DNA so that the ratios of the wheat DNA to the salmon sperm DNA were 0.1 ppm, 10 ppm, 50 ppm, 100 ppm, 1,000 ppm and 1% by volume. Alternatively, the artificially mixed samples at the powder level were prepared by mixing wheat flour and maize flour so that the mixed ratios of wheat flour to maize flour were 0.1 ppm, 10 ppm, 50 ppm, 100 ppm, 1,000 ppm, and 1% by weight. Subsequently, each mixed sample was finely ground, and then DNA was extracted.

Figure 2A:
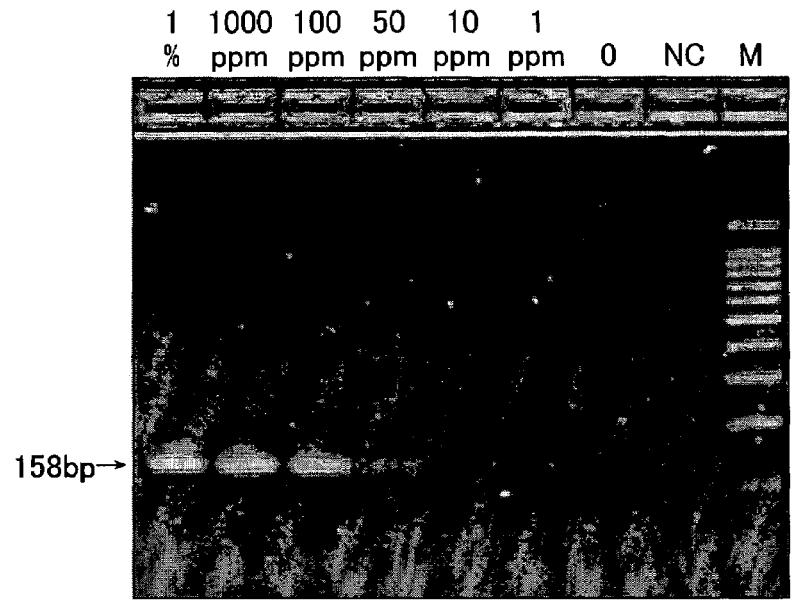
FIG. 2a shows measurement of artificially mixed samples of DNA level.
Figure 2B:
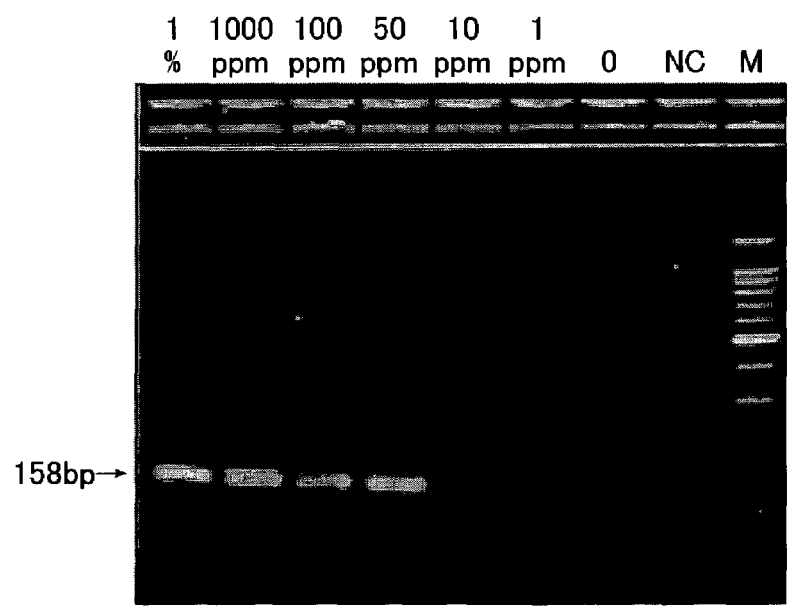
FIG. 2b is an electrophorogram showing measurement of artificially mixed samples of powder level.

FIGS. 2a and 2b are electrophorograms showing results of the detection. Upper numerals indicate the content of wheat, and M represents 100 bp ladder and NC represents no template control (blank without template DNA). In FIG. 2a, the samples at the DNA level prepared by diluting the wheat DNA with the salmon sperm DNA were used for the analyte. In FIG. 2b, the samples at the powder level prepared by diluting the wheat flour with the maize flour were used for the analyte.

In the experiment 2-1, the detection limit of wheat by PCR using Wgs 11 (SEQ ID NO:9)/Wgs 12 (SEQ ID NO:10) was identified. Results show that the detection limit of wheat in both the samples at the DNA and powder levels was 50 ppm (FIG. 2). In the experiments repeated multiple times, however, the detection limit was 100 ppm in several experiments, and thus, it has been suggested that the limit stably detectable by this PCR system is 100 ppm. The protein content in the wheat flour is about 10% by weight (according to the Food Composition Table, 5th edition), and thus, 100 ppm of the detection limit by the PCR corresponds to 10 ppm of the mixing ratio of the wheat protein.

Accordingly, it is expected that the method for detecting wheat by the PCR as described above is capable of attaining a higher detection limit than before and allowing reliable measurement (analysis) of a trace component with high specificity.

(5-2) Experiment 2-2. Identification of Detection Limit of Wheat by PCR

In Experiment 2-2, for the purpose of examining the detection limit of wheat by PCR using the primers Wss 01 (SEQ ID NO:1)/Wss 02 (SEQ ID NO:12), artificially mixed samples of wheat at DNA level were prepared according to the Experiment 2-1, and PCR was performed using those DNA samples to identify the detection limit of wheat.

Figure 4:
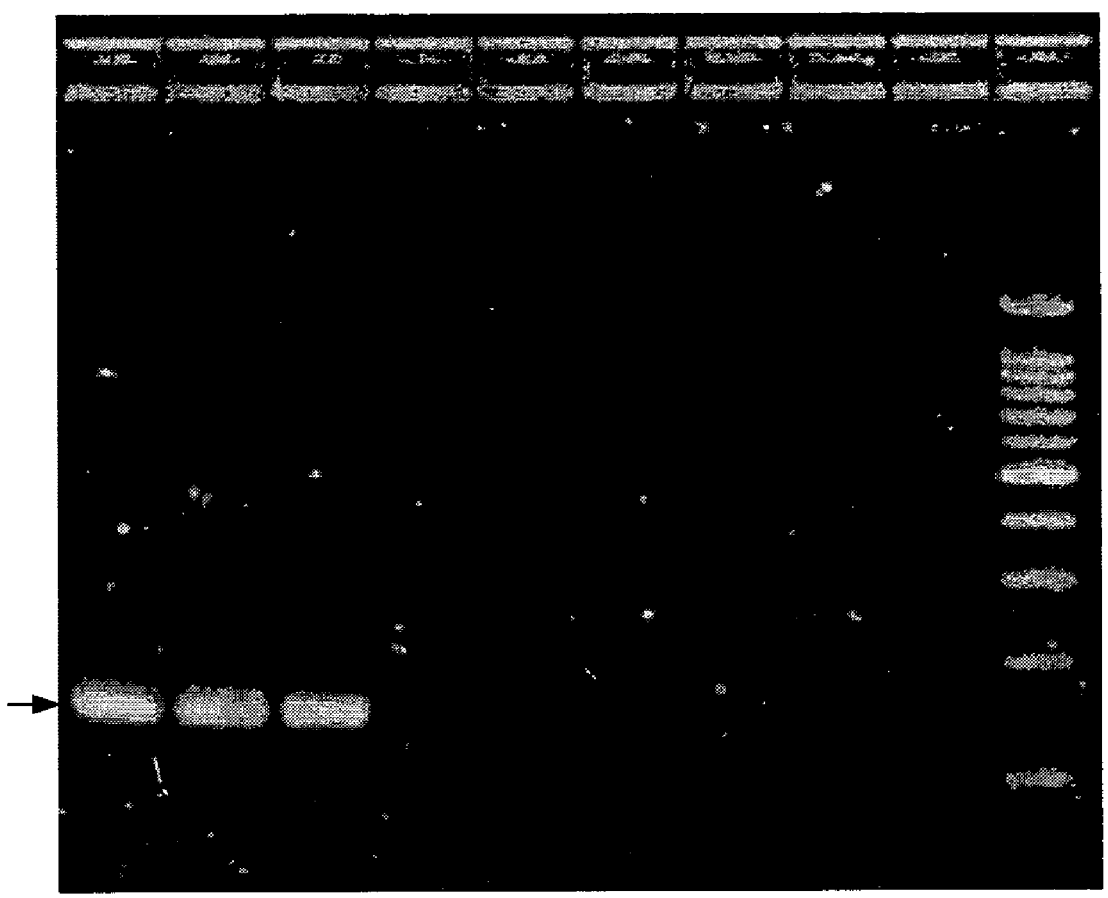
FIG. 4 shows an electrophorogram for the results by a wheat detection system using PCR.

FIG. 4 is an electrophorogram showing results of the detection. Upper numerals indicate content of wheat. M represents 100 bp ladder and NC represents no template control (blank without template DNA). In FIG. 4, the samples at DNA level in which wheat DNA was diluted with salmon sperm DNA were used for the analyte.

(6) Experiment 3. Detection of Wheat in Processed Foods by PCR

The detection of wheat was performed from processed foods containing wheat as a raw material using Wgs 11 (SEQ ID NO:9)/12 (SEQ ID NO:10) as the primers. Samples used were a retort can, cake mix, spaghetti, cereals, and 7 kinds of confectionery (biscuit, rice cracker, pretzel, gluten bread, sponge cake, snack, chocolate). Each was finely ground, and then DNAs were extracted using Dneasy Plant Maxi kit or Genomic Tip 20/G (Qiagen) and the extracted DNAs were subjected to the PCR. Since the purity of the resulting DNA extracted from the retort can was low, 50 to 120 ng of the DNA (as calculated from the absorbance) per tube was used for the PCR reaction.

Figure 3A:
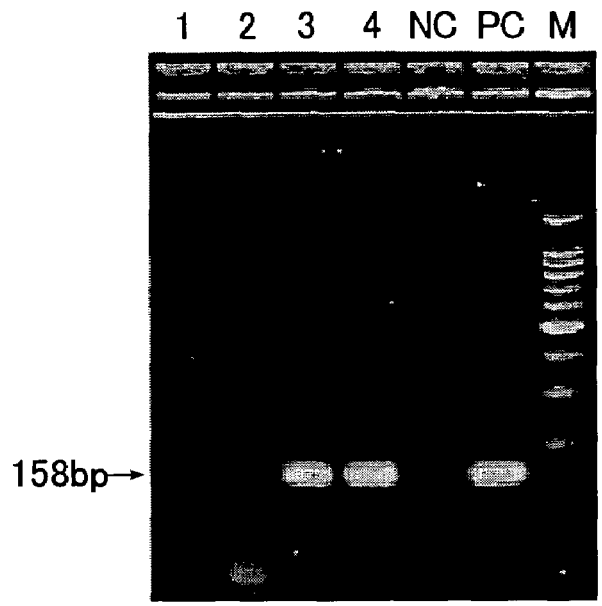
FIG. 3 is an electrophorogram showing results of detection of wheat in processed foods by PCR. The kinds of the processed foods measured in FIGS. 3a and 3b are different from one lane to another.
Figure 3B:
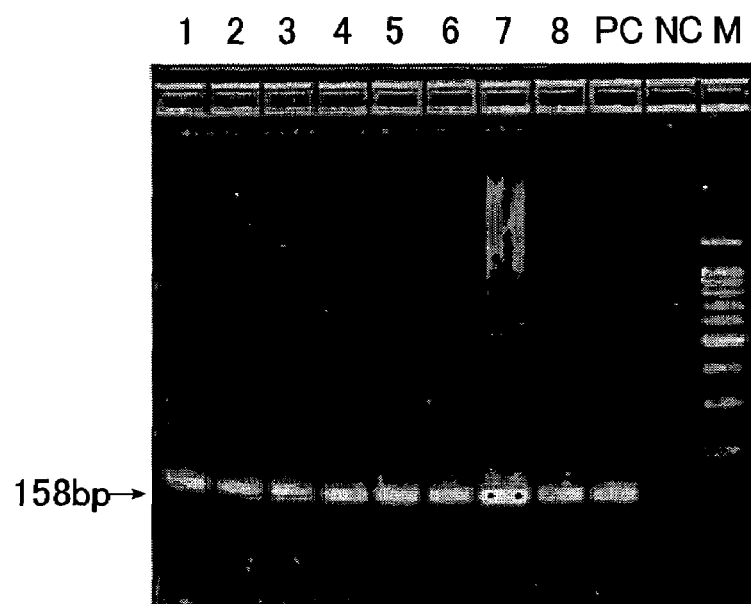

Table 4 shows lane numbers (sample names) in FIGS. 3a and 3b.

TABLE 4

| Lane number | | Sample name |
|---|---|---|
| FIG. 3a | 1 | Retort can (template DNA: 50 ng/tube) |
| | 2 | Retort can (template DNA: 120 ng/tube) |
| | 3 | Cake mix |
| | 4 | Spaghetti |
| | NC | Water |
| | PC | Wheat |
| | M | 100 bp ladder |
| FIG. 3b | 1 | Cereals |
| | 2 | Biscuit |
| | 3 | Rice cracker |
| | 4 | Pretzel |
| | 5 | Gluten bread |
| | 6 | Sponge cake |
| | 7 | Snack |
| | 8 | Chocolate |
| | PC | Wheat |
| | NC | Water |
| | M | 100 bp ladder |

The detection of wheat from the processed foods was performed by the PCR using Wgs 11 (SEQ ID NO:9)/12 (SEQ ID NO:10) (Experiment 3). As a result, the wheat was detected from the samples except the retort can (FIG. 3). No wheat was detected from the retort can even when the template DNA was added up to 50 ng or 120 ng (FIG. 3a). It has been supposed that the retort can is subjected to the retorting at 120° C. for about 30 min, so that the DNA was finely fragmented during the heating and the detection by the PCR could not be achieved.

Food allergy tests currently carried out in the clinical settings include provocative test, skin prick test and RAST method. However, the targets in the tests by these methods are patients suffering from allergies or blood thereof and it is difficult to apply these methods to food analysis. On the other hand, electrophoresis (SDS-PAGE), western blotting, and immunochemical methods (ELISA) have been used for isolating and detecting a specific protein for the purpose of detecting and quantifying an allergen per se and these methods are effective for the detection of known major allergens. However, these methods are not necessarily appropriate for the detection of unknown allergens or in processed foods in which proteins may be potentially denatured by heating.

INDUSTRIAL APPLICABILITY

DNAs very often remain in processed foods because of their higher heating resistance than proteins. Therefore, the method for detecting a wheat gene by PCR according to the present invention is significantly useful particularly in processed foods as a means for indirectly analyzing an allergic substance in a food, which compensates for conventional protein detection methods.

The invention claimed is:

1. A method for detecting the presence of wheat in a food, comprising the steps of:
   extracting DNA from the food;
   performing PCR using the extracted DNA as a template and a primer pair of Wtr01 consisting of the nucleic acid sequence of SEQ ID NO: 1 and Wtr10 consisting of the nucleic acid sequence of SEQ ID NO: 2, wherein said primer pair is specific for wheat; and
   detecting whether wheat is present by identifying a PCR product indicating at least one species of wheat.

2. The method according to claim 1, wherein said method is for identifying whether a food contains a wheat allergen.

3. The method according to claim 1, wherein the food comprises a processed food or a food raw material.

4. The method according to claim 1, further comprising a step of electrophoresis to determine whether said wheat is present.

5. The method according to claim 1, wherein the PCR-product is identified by electrophoresis.

6. The method according to claim 1, wherein the method is capable of detecting 50 ppm or more of wheat in a total amount of food.

* * * * *